US00PP16785P2

(12) United States Plant Patent
Iwaki et al.

(10) Patent No.: US PP16,785 P2
(45) Date of Patent: Jul. 11, 2006

(54) ***PETUNIA* PLANT NAMED 'KEIPAWHIHIS'**

(50) Latin Name: *Petunia×hybrida*
Varietal Denomination: Keipawhihis

(75) Inventors: Kazunari Iwaki, Shiga (JP); Shinya Miyano, Tounosyou-machi (JP)

(73) Assignees: Keisei Rose Nurseries, Inc., Tokyo (JP); Suntory Flowers Ltd., Tokyo (JP)

( * ) Notice: Subject to any disclaimer, the term of this patent is extended or adjusted under 35 U.S.C. 154(b) by 28 days.

(21) Appl. No.: 11/091,845

(22) Filed: Mar. 28, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP14,748 P2 * 5/2004 Miyano ..... Plt./356

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Petunia* plant named 'Keipawhihis', characterized by its upright and mounded plant habit; vigorous and freely branching growth habit; freely flowering habit; white to light purple bi-colored flowers; long flowering period; and good garden performance.

1 Drawing Sheet

Botanical designation: *Petunia×hybrida.*
Cultivar denomination: 'Keipawhihis'.

BACKGROUND OF THE INVENTION

The present Invention relates to a new and distinct cultivar of *Petunia* plant, botanically known as *Petunia×hybrida,* and hereinafter referred to by the cultivar name Keipawhihis.

The new *Petunia* is a product of a planned breeding program conducted by the Inventors in Sawara, Chiba, Japan. The objective of the breeding program is to create new *Petunias* with numerous flowers with attractive flower colors.

The new *Petunia* originated from a cross-pollination made by the Inventors in September, 2001 of two unidentified proprietary *Petunia* selections, not patented. The new *Petunia* was selected as a single plant from the resulting progeny of the cross-pollination by the Inventors in a controlled environment in Yokaichi, Shiga, Japan.

Asexual reproduction of the new cultivar by terminal cuttings in a controlled environment in Sawara, Chiba, Japan since September, 2003 has shown that the unique features of this new *Petunia* are stable and reproduced true to type in successive generations.

SUMMARY OF THE INVENTION

Plants of the cultivar Keipawhihis have not been observed under all possible environmental conditions. The phenotype may vary somewhat with variations in environment such as temperature and light intensity without, however, any variance in genotype.

The following traits have been repeatedly observed and are determined to be the unique characteristics of 'Keipawhihis'. These characteristics in combination distinguish 'Keipawhihis' as a new and distinct *Petunia* cultivar:

1. Upright and mounded plant habit.
2. Vigorous and freely branching growth habit.
3. Freely flowering habit.
4. White to light purple-colored flowers.
5. Long flowering period.
6. Good garden performance.

Plants of the new *Petunia* differ from plants of the female parent selection in the following characteristics:

1. Plants of the new *Petunia* are shorter and narrower than plants of the female parent selection.
2. Plants of the new *Petunia* and the female parent selection differ in petal coloration as plants of the female parent selection have red purple-colored petals.

Plants of the new *Petunia* differ from plants of the male parent selection in the following characteristics:

1. Plants of the new *Petunia* are taller and broader than plants of the male parent selection.
2. Plants of the new *Petunia* have larger flowers than plants of the male parent selection.

Plants of the new *Petunia* can be compared to plants of the cultivar Keipabukas, disclosed in U.S. Plant Pat. No. 14,748. In side-by-side comparisons conducted in Sawara, Chiba, Japan, plants of the new *Petunia* differed from plants of the cultivar Keipabukas in the following characteristics:

1. Plants of the new *Petunia* had larger flowers than plants of the cultivar Keipabukas.
2. Plants of the new *Petunia* and the cultivar Keipabukas differed in flower throat and tube coloration.
3. Plants of the new *Petunia* flowered longer than plants of the cultivar Keipabukas.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a side perspective view of a typical flowering plant of 'Keipawhihis' grown in a container.

The photograph at the bottom of the sheet comprises a close-up view of typical flowers of 'Keipawhihis'.

DETAILED BOTANICAL DESCRIPTION

The aforementioned photographs and following observations and measurements describe plants grown in Sawara, Chiba, Japan, in 24-cm containers for about three months in an outdoor nursery during the summer with day temperatures about 27° C. and night temperatures about 20° C. Plants were pinched one time in the early summer. Color references are made to The Royal Horticultural Society Colour Chart, 2001 Edition, except where general terms of ordinary dictionary significance are used.

Botanical classification: *Petunia×hybrida* cultivar Keipawhihis.

Parentage:

*Female, or seed, parent.*—Unidentified proprietary *Petunia* selection, not patented.

*Male, or pollen, parent.*—Unidentified proprietary *Petunia* selection, not patented.

Propagation:

*Type cutting.*—Terminal vegetative cuttings.

*Time to initiate roots.*—About one week at 20° C. to 25° C.

*Time to develop roots.*—About three weeks at 20° C. to 25° C.

*Root description.*—Fine, fibrous, fleshy; light brown in color.

*Rooting habit.*—Freely branching.

Plant description:

*Plant and growth habit.*—Annual flowering plant; indeterminate; upright and mounded plant habit. Viscid and glandular pubescent. Vigorous growth habit. Freely branching habit with lateral branches developing potentially at every node.

*Plant height.*—About 20 cm.

*Plant diameter.*—About 40 cm.

*Lateral branches.*—Length: About 25 cm. Diameter: About 2 mm. Internode length: About 1 cm. Texture: Pubescent. Color: 144B.

*Foliage description.*—Arrangement: Alternate, simple; sessile. Length: About 4.5 cm. Width: About 3 cm. Shape: Elliptic. Apex: Obtuse. Base: Cuneate. Margin: Entire. Texture, upper and lower surfaces: Sparsely pubescent; viscid. Venation pattern: Pinnate; reticulate. Color: Developing and fully expanded foliage, upper surface: 144A. Developing and fully expanded foliage, lower surface: 144B. Venation, upper and lower surfaces: Similar to lamina.

Flower description:

*Flower type and habit.*—Single salverform flowers; flowers face mostly upward or outward; axillary. Flowers not persistent. Freely flowering habit.

*Natural flowering season.*—Long flowering period, plants flower from spring through late autumn in Japan; flowering continuous during this period.

*Flower longevity on the plant.*—About five days.

*Fragrance.*—Faint.

*Flower size.*—Diameter: About 4.5 cm. Length: About 3.5 cm.

*Flower buds.*—Length: About 2 cm. Diameter: About 7 mm. Shape: Cylindrical. Color: 154A.

*Corolla.*—Quantity/arrangement: Five petals; fused, funnelform. Petal length: About 2 cm. Petal width: About 1.5 cm. Petal shape: Roughly spatulate or fan-shaped. Petal apex: Cuspidate. Petal margin: Entire; slightly undulate. Petal texture, upper and lower surfaces: Smooth; satiny. Color: Petal, when developing and fully expanded, upper surface: 155D; color becoming closer to 75D with development. Petal, when developing and fully expanded, lower surface: 155A. Flower throat (inside): 4D; venation, 151C. Flower tube (outside): 154C; venation, 144B.

*Sepals.*—Arrangement/appearance: Single whorl of five sepals fused at base, star-shaped. Length: About 1 cm. Width: About 2 mm. Shape: Narrowly oblong. Apex: Rounded. Margin: Entire. Texture, upper and lower surfaces: Pubescent. Color, immature, upper and lower surfaces: 144B. Color, mature, upper surface: 144A. Color, mature, lower surface: 144B.

*Peduncles.*—Length: About 1.5 cm. Width: About 1 mm. Strength: Moderately strong. Texture: Pubescent; viscid. Color: 144B.

*Reproductive organs.*—Stamens: Quantity: Five per flower. Anther shape: Ellipsoidal. Anther size: About 2 mm by 1.4 mm. Anther color: 4D. Pollen amount: Moderate. Pollen color: 4D. Pistils: Quantity: One per flower. Pistil length: About 1.4 cm. Style length: About 1.3 cm. Style color: 143D. Stigma shape: Elliptic. Stigma color: 143B. Ovary color: 143C.

*Seeds.*—Diameter: About 0.5 mm. Color: N186C.

Disease/pest resistance: Plants of the new *Petunia* have not been noted to be resistant to specific pathogens and pests common to *Petunia*.

Garden performance: Plants of the new *Petunia* have been observed to have good garden performance and tolerate rain, wind and tolerated temperatures from 5° C. to 35° C.

It is claimed:

1. A new and distinct cultivar of *Petunia* plant named 'Keipawhihis', as illustrated and described.

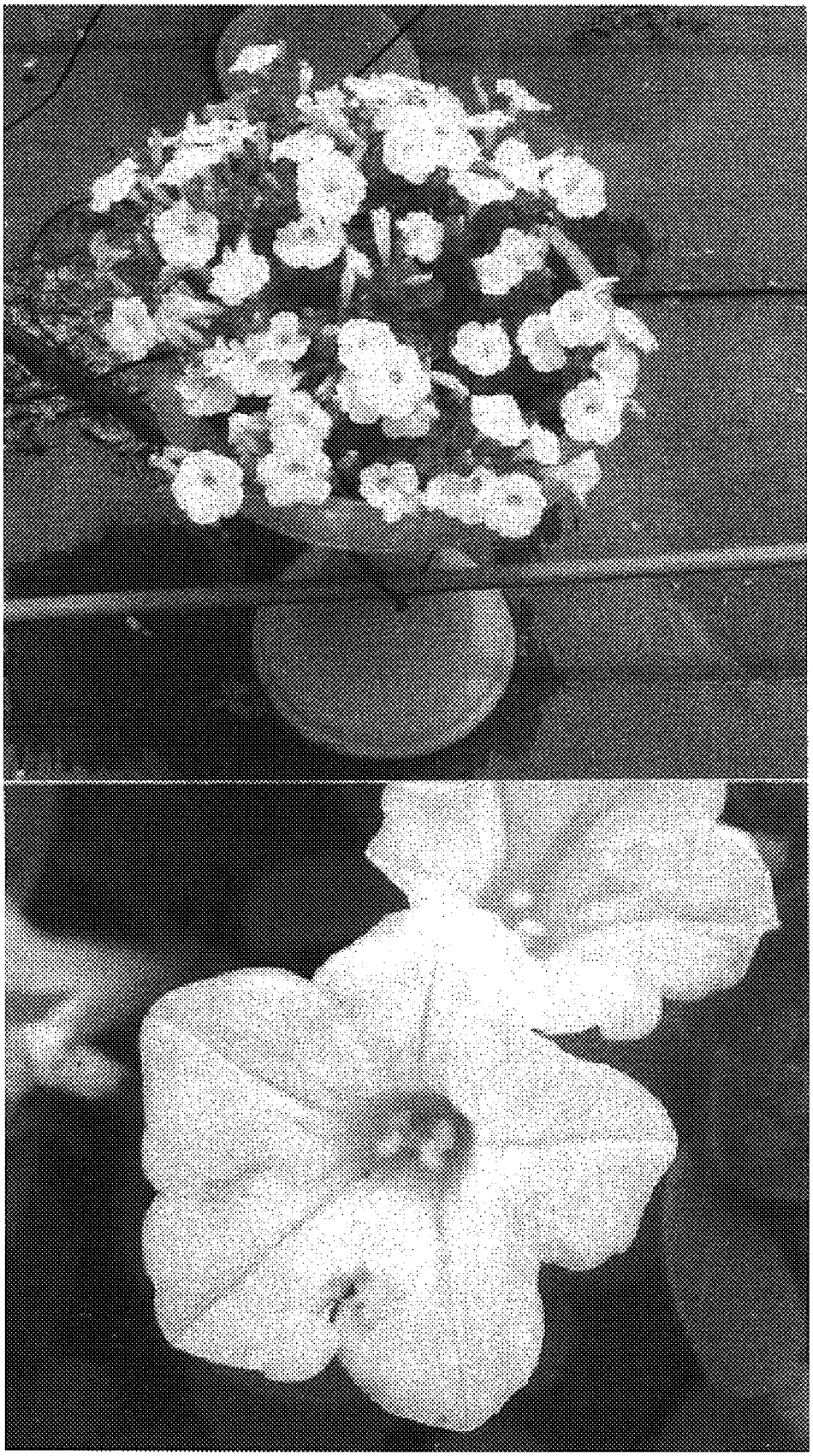

* * * * *